United States Patent [19]

Bowen

[11] Patent Number: 5,792,213
[45] Date of Patent: Aug. 11, 1998

[54] HOT OR COLD CHEMICAL THERAPY PACK

[75] Inventor: Michael L. Bowen, Arlington, Tex.

[73] Assignee: Tecnol Medical Products, Inc., Fort Worth, Tex.

[21] Appl. No.: 559,469

[22] Filed: Nov. 15, 1995

[51] Int. Cl.$^6$ .................................................. A61F 7/00
[52] U.S. Cl. ......................................... 607/96; 607/114
[58] Field of Search ............................ 607/96, 99, 104, 607/108, 109–114

[56] References Cited

U.S. PATENT DOCUMENTS

| | | | |
|---|---|---|---|
| 2,589,577 | 3/1952 | Rosenthal et al. | 62/1 |
| 2,898,744 | 8/1959 | Robbins | 62/4 |
| 2,907,173 | 10/1959 | Robbins | 62/4 |
| 3,095,291 | 6/1963 | Robbins | 62/4 |
| 3,149,943 | 9/1964 | Amador | 62/4 |
| 3,191,392 | 6/1965 | Donnelly | 62/4 |
| 3,491,761 | 1/1970 | Baker | 128/402 |
| 3,542,032 | 11/1970 | Spencer, Jr. | 128/399 |
| 3,608,709 | 9/1971 | Pike | 206/47 A |
| 3,736,769 | 6/1973 | Petersen | 62/530 |
| 3,749,620 | 7/1973 | Montgomery | 156/73 |
| 3,763,622 | 10/1973 | Stanley, Jr. | 53/25 |
| 3,785,111 | 1/1974 | Pike | 53/14 |
| 3,807,118 | 4/1974 | Pike | 53/14 |
| 3,847,279 | 11/1974 | Montgomery | 206/219 |
| 3,865,117 | 2/1975 | Perry, III | 128/403 |
| 3,893,834 | 7/1975 | Armstrong | 62/4 |
| 3,950,158 | 4/1976 | Gossett | 62/4 |
| 4,000,996 | 1/1977 | Jordan | 62/4 |
| 4,033,354 | 7/1977 | De Rosa | 128/379 |
| 4,044,773 | 8/1977 | Baldwin, III | 128/402 |
| 4,057,047 | 11/1977 | Gossett | 126/263 |
| 4,077,390 | 3/1978 | Stanley et al. | 126/263 |
| 4,081,150 | 3/1978 | Tyson | 128/402 |
| 4,081,256 | 3/1978 | Donnelly | 62/4 |
| 4,204,543 | 5/1980 | Henderson | 128/402 |
| 4,326,533 | 4/1982 | Henderson | 128/402 |
| 4,347,848 | 9/1982 | Hubbard et al. | 128/402 |
| 4,372,318 | 2/1983 | Viesturs et al. | 128/403 |
| 4,385,950 | 5/1983 | Hubbard et al. | 156/73.1 |
| 4,397,315 | 8/1983 | Patel | 128/403 |
| 4,402,402 | 9/1983 | Pike | 206/219 |
| 4,427,010 | 1/1984 | Marx | 128/402 |
| 4,462,224 | 7/1984 | Dunshee et al. | 62/530 |
| 4,523,353 | 6/1985 | Hubbard et al. | 24/30.5 |
| 4,527,566 | 7/1985 | Abare | 128/402 |
| 4,537,184 | 8/1985 | Williams, Jr. | 128/90 |
| 4,585,003 | 4/1986 | Meistrell | 128/402 |
| 4,586,506 | 5/1986 | Nangle | 128/403 |

(List continued on next page.)

FOREIGN PATENT DOCUMENTS

| | | | |
|---|---|---|---|
| 1263581 | 12/1989 | Canada | A61F 7/08 |
| 474249 | 10/1937 | United Kingdom . | |

*Primary Examiner*—John P. Lacyk
*Attorney, Agent, or Firm*—Baker & Botts, L.L.P.

[57] ABSTRACT

A hot or cold chemical therapy pack (1) is provided that has two compartments (28, 30). One compartment (28) has a natural weak point (32) or seam (at 24 or 26) and is contained inside the other compartment (30). Each compartment contains a chemical reactant. In one embodiment, the outer compartment (30), which is made of a flexible, vinyl or plastic material, is arranged in a semi-collapsed configuration. Each end of the inner compartment (28) is fixedly attached to a respective end (24, 26) of the outer compartment (30). The pack (10) is chemically activated by pressing on, kneading, or twisting the outer compartment (30), or pulling on each end of the pack (10). The lateral, outward pressure caused by the pressing on, kneading, or twisting of the pack, or by the user's pulling on the ends of the pack, is exerted at the rupturable seam (32) of the inner compartment (28). At a predetermined pressure, the natural weak point (32) or seam is ruptured and the reactant contents of the two compartments merge (34), which creates the heating (exothermic) or cooling (endothermic) chemical reaction. Consequently, the hot or cold chemical therapy pack (10) is more easily activated than existing chemical therapy packs, which makes this pack (10) more convenient to use.

24 Claims, 2 Drawing Sheets

U.S. PATENT DOCUMENTS

| | | | |
|---|---|---|---|
| 4,628,932 | 12/1986 | Tampa | 128/402 |
| 4,636,391 | 1/1987 | Pike | 426/106 |
| 4,668,564 | 5/1987 | Orchard | 428/246 |
| 4,688,572 | 8/1987 | Hubbard et al. | 128/402 |
| 4,751,119 | 6/1988 | Yukawa | 428/35 |
| 4,780,117 | 10/1988 | Lahey et al. | 62/4 |
| 4,805,620 | 2/1989 | Meistrell | 128/402 |
| 4,854,760 | 8/1989 | Pike et al. | 401/134 |
| 4,856,651 | 8/1989 | Francis, Jr. | 206/219 |
| 4,931,333 | 6/1990 | Henry | 428/76 |
| 4,951,666 | 8/1990 | Inman et al. | 128/402 |
| 4,953,550 | 9/1990 | Dunshee | 128/403 |
| 4,972,832 | 11/1990 | Trapini et al. | 128/402 |
| 4,986,076 | 1/1991 | Kirk et al. | 62/4 |
| 5,020,711 | 6/1991 | Kelley | 224/222 |
| 5,045,041 | 9/1991 | Murphy | 493/194 |
| 5,074,300 | 12/1991 | Murphy | 128/402 |
| 5,163,504 | 11/1992 | Resnick | 165/47 |
| 5,178,139 | 1/1993 | Angelillo et al. | 128/403 |
| 5,184,470 | 2/1993 | Moser et al. | 62/4 |
| 5,205,278 | 4/1993 | Wang | 126/263 |
| 5,261,241 | 11/1993 | Kitahara et al. | 62/4 |
| 5,275,156 | 1/1994 | Milligan et al. | 607/114 |
| 5,356,426 | 10/1994 | Delk et al. | 607/112 |
| 5,466,251 | 11/1995 | Brunson et al. | 607/112 |

HOT OR COLD CHEMICAL THERAPY PACK

TECHNICAL FIELD OF THE INVENTION

The present invention relates generally to the field of hot and cold therapy devices, and more specifically, to a hot or cold chemical therapy pack that can be readily activated.

BACKGROUND OF THE INVENTION

Cold therapy is an established practice used in the medical profession to treat certain limb injuries, such as, for example, sprained or strained arm or leg muscles, or injuries to joints. Generally, these types of injuries should be chilled to slow blood flow, which reduces swelling, pain, and further damage. A typical course of cold therapy treatment is to apply ice for a specified period to the injured region of the limb. Alternatively, a pack or bag containing a chemical agent that reacts (endothermically) to produce cold may be applied to the injured region.

Heat therapy may be used, in other circumstances, to warm up or limber muscles by increasing blood flow. For example, athletes may apply heat with a hot water bag for a specified period to thighs or calf muscles prior to an event. Alternatively, a pack or bag containing a chemical agent that reacts (exothermically) to produce heat may be applied to the region of interest.

A number of devices that use endothermic or exothermic reactions for cooling or heating body parts are known. For example, U.S. Pat. No. 4,986,076 to Kirk et al. and U.S. Pat. No. 2,898,744 to Robbins both disclose a flexible, plastic cooling bag sealed along its edges. The cooling bag is separated by a frangible barrier into two portions: a freezing chemical mixture (salt) portion and a liquid (water) portion. A cooling reaction is activated by squeezing or applying pressure to the bag, which ruptures the frangible barrier and thus allows the salt and liquid portions to mix. The resulting chemical mixture causes an endothermic reaction, which produces a cooling effect. The cooled bag is applied to a body part. Separate bags are used for cooling and heating.

In yet another exothermic application, a small, plastic heat pack commonly referred to as a "heel warmer" chemically activated and placed against the foot of a newborn infant to raise or maintain the infant's body temperature. Similar to the above-described heat or cold packs, the heel warmer's heating reaction is also activated by squeezing or applying pressure to the pack, in order to rupture the frangible barrier between the reactants. Alternatively, a heel warmer's reaction can be activated by a so-called "trigger" device.

Various types of "trigger" devices have been used to initiate the heating or cooling reaction. For example, U.S. Pat. No. 5,275,156 to Milligan et al. discloses a reusable heat pack containing a liquid reactant, such as sodium acetate tetrahydrate, which releases heat upon crystallization. A "trigger" located within the pack is used to initiate the liquid's crystallization. The trigger is a hollow receptacle composed of a flexible, plastic material. The receptacle holds a plurality of spherical ceramic or glass objects. The glass or ceramic spherical objects in the receptacle are compressed or squeezed between the user's fingers, which causes the objects to rub together and initiate the crystallization process.

In U.S. Pat. No. 5,205,278 to Wang, a chemical bag warmer is disclosed which also uses a "trigger" device to initiate the exothermic reaction. A flexible plastic bag is filled with a sodium acetate solution. A "triggering member," which is a flexible metal disc, is bent up and down inside the sodium acetate solution. The metal disc, when bent up and down, is adapted to vibrate and generate an oscillation sound wave. The oscillation wave triggers the sodium acetate solution to crystallize and release heat. However, similar to the compression type activation processes used for other conventional packs, the "trigger" process of activating chemical hot or cold packs is relatively cumbersome and inconvenient to use.

Accordingly, a need has arisen for a hot or cold chemical therapy pack that is relatively easy to activate.

SUMMARY OF THE INVENTION

In accordance with a preferred embodiment of the present invention, a hot or cold chemical therapy pack is provided that has two compartments. One compartment is rupturable, in that it has a rupturable seam or a natural weak point and is contained inside the other compartment. Each compartment contains a chemical reactant. In one embodiment, the outer compartment, which is made of a flexible, vinyl or plastic material, is arranged in a semi-collapsed configuration. Each end of the inner compartment is fixedly attached to a respective end of the outer compartment. The pack is chemically activated by pressing on, kneading, or twisting the outer compartment, or pulling on each end of the pack. The lateral, outward pressure caused by the pressing on, kneading, or twisting of the pack, or by the user's pulling on the ends of the pack, is exerted on the seam or weak point in the inner compartment. At a predetermined pressure, the seam or weak point in the inner compartment is ruptured and the reactant contents of the two compartments merge, which creates the heating (exothermic) or cooling (endothermic) chemical reaction.

An important technical advantage of the present invention is that the hot or cold chemical therapy pack is more easily activated than existing chemical therapy packs, which makes this pack more convenient to use.

DETAILED DESCRIPTION OF THE INVENTION

The preferred embodiment of the present invention and its advantages are best understood by referring to FIGS. 1–4 of the drawings, like numerals being used for like and corresponding parts of the various drawings.

Figure 1:
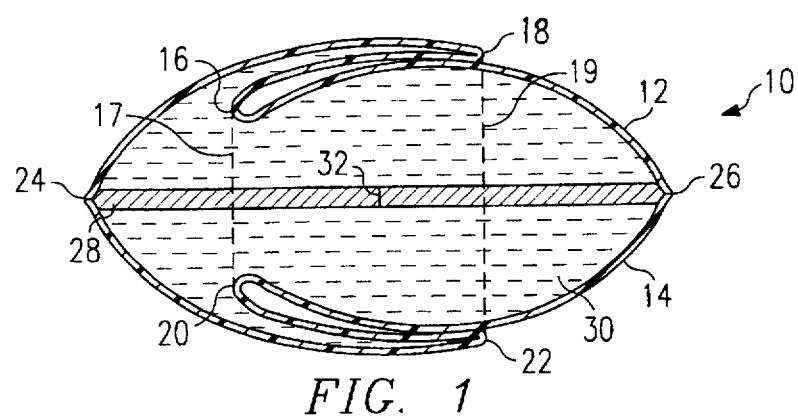
FIG. 1 is a side view of a hot or cold chemical therapy pace according to a preferred embodiment of the present invention.

FIG. 1 is a side view of a hot or cold chemical therapy pack structured in accordance with a preferred embodiment of the present invention. Referring to FIG. 1, pack 10 may be applied to a human or animal body part, or even used for other hot or cold applications, such as, for example, heating or cooling drinks and foodstuffs. Pack 10 is constructed with a pair of substantially rectangular-shaped sheets 12 and 14 of a relatively flexible, plastic or vinyl film material. For example, each of sheets 12 and 14 can be a film of material made of polyethylene, polypropylene or polyvinylchloride. However, the material composition of sheets 12 and 14 is not intended to act as a limitation on the scope of the present invention. Essentially, sheets 12 and 14 can be made of any one of a number of relatively strong, but pliable materials known and used in the heat or cold therapy art.

Sheets 12 and 14 are sealed to each other, along their peripheries, by a relatively strong heat seal. Although heat sealing of these sheets is preferable, any method of mechanically sealing sheets 12 and 14 along their peripheries can be used, such as, for example, an RF seal, ultrasonic seal, glue, etc. Preferably, sheets 12 and 14 are sealed to form a single compartment 30. Therefore, in the embodiment shown in FIG. 1, pack 10 is formed substantially in the shape of a bean-bag. In any event, although pack 10 is shown in FIG. 1 as substantially "bean-bag shaped," the invention is not intended to be limited to any particular shape or dimension, so pack 10 can be any practical size or shape. For example, pack 10 can be oval-shaped, substantially circular in shape, or substantially rectangular in shape with rounded corners. An example of such a rectangularly shaped pack is shown in commonly-assigned U.S. patent application Ser. No. 08/403, 295 filed Mar. 14, 1995, the text and figures of which are incorporated herein by reference.

Pack 10 is preferably a liquid-filled vinyl or plastic bag. However, considering a different aspect of the invention, compartment 30 can be filled with a solid, chemical reactant, such as a reactant powder, or a plurality of water soluble, exothermic or endothermic beads or "prills." For example, in one embodiment, compartment 30 is filled with a liquid reactant (e.g., a solvent) composed primarily of water. A salt or other appropriate chemical can be added to the liquid solvent to lower the freezing point of the water, in order to keep the water from freezing prior to activation. The liquid reactant can also be one of a number of known liquid reactants such as, for example, a mixture of water and aqueous ammonia.

During the initial fabrication of pack 10, compartment 30 is partially filled with the liquid or solid reactant. As illustrated by FIG. 1, opposing ends 24 and 26 of pack 10 are compressed towards each other, and sheets 12 and 14 are thereby formed with folds 16 and 18 (sheet 12), and folds 20 and 22 (sheet 14). Folds 16 and 20 overlap to form a first continuous fold 18 around the periphery of pack 10, and folds 18 and 22 overlap to form a second continuous fold 19 around the periphery of the pack. Pack 10 is thus constructed, for example, in a semi-collapsed configuration. Also during the initial fabrication of pack 10, the opposing ends of tubular compartment 28 are attached to, and sealed at, opposing ends 24 and 26 of the pack. For the embodiment wherein compartment 30 is partially filled with a liquid reactant, tubular compartment 28 can be filled with a complementary liquid or solid reactant which, when combined with the reactant in compartment 30, creates an exothermic (heating) or endothermic (cooling) chemical reaction in pack 10. For an endothermic reaction, tubular compartment 28 can be filled with a plurality of water soluble, spherically shaped beads (e.g., prills) that are capable of being dissolved in the water, preferably beads of ammonium nitrate. Alternatively, for an exothermic reaction (heating), the water soluble, spherically shaped beads in tubular compartment 28 can be made of calcium chloride. Compartment 28 can contain prills or some structural and chemical equivalent of prills. For example, these water soluble beads could be very small particles arranged to form a "slurry." Examples of materials that can be used for exothermal reactants include quick lime, sodium hydroxide, cobalt, chromium, iron, iron hydroxide, magnesium, manganese, molybdenum, tin oxide(II), titanium, sodium, sodium acetate crystals, calcium hydroxide, metallic sodium, magnesium chloride and anhydrous calcium chloride ($CaCl_2$). Examples of materials that can be used for endothermal reactions include ammonium nitrate ($NH_4NO_3$), and salts such as ammonium sulfurate, potassium nitrate and sodium thiosulfate. In a second embodiment of the invention, compartment 28 may contain the water or mixture of water and aqueous ammonia, or a super-cooled sodium acetate solution, while compartment 30 contains the complementary reactant (e.g., water soluble beads, etc.). Tubular compartment 28 is preferably rupturable and may be constructed of a relatively flexible, plastic or vinyl material having a natural weak point 32 (e.g., a rupture can occur at a naturally weak point anywhere in the wall of the tubular compartment and is not necessarily location dependent). Alternatively, rupturable tubular compartment 28 can be constructed of a relatively rigid material that can be ruptured with substantial pressure at a seam at sealed end 24 or 26. Alternatively, by way of example, each of sheets 12 and 14 can be a square or rectangular sheet sealed to the other to form a shape similar to a bean-bag. In any event, although compartment 28 is described with respect to one aspect of the invention as tubular in shape, the invention is not intended to be limited to any particular shape or dimension for this inner compartment, so compartment 28 can be any practical size or shape. For example, compartment 28 can be substantially rectangular in shape.

Figure 2:
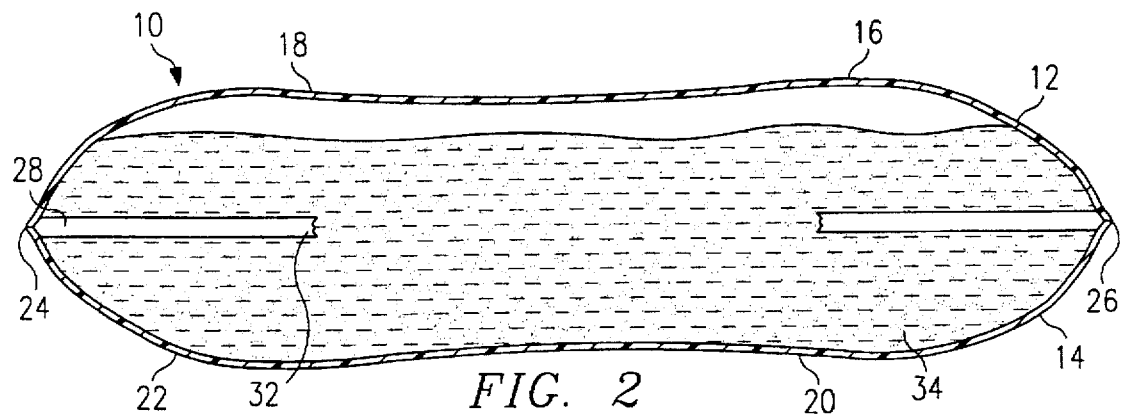
FIG. 2 is a side view of the hot or cold chemical therapy pace shown in FIG. 1 after the inner compartment has ruptured or broken at a weak point.

FIG. 2 is a side view of the hot or cold chemical therapy pack shown in FIG. 1 after the inner compartment has ruptured or broken at a weak point (indicated for illustrative purposes at location 32). Referring to FIGS. 1 and 2, in order to activate pack 10 for use, tubular compartment 28 is ruptured at location 32 by pulling ends 24 and 26 apart (e.g., leftward and rightward, respectively, in FIGS. 1 and 2). Alternatively, compartment 28 can be ruptured by applying pressure to, squeezing, or kneading compartment 30, so that the external pressure applied to compartment 30 is transferred to ends 24 and 26, respectively, in the leftward and rightward directions in FIG. 2. Once a substantial amount of lateral pressure is reached at weak point 32 (or a seam at 24 or 26), the seam or weak point is ruptured (FIG. 2) and the contents of compartments 28 and 30 are thus merged (solution 34) and mix together to react. Consequently, the desired endothermic or exothermic reaction is activated and pack 10 creates either a cooling or heating effect. Pack 10 can then be placed against the body part or item to be cooled or heated. Alternatively, during the initial fabrication of pack 10, compartment 20 can be attached to ends 24 and 26 so that at least one of the seals at the ends of compartment 28 is rupturable. Consequently, when the external pressure applied to compartment 30 is transferred laterally to ends 24 and 26, respectively, in the leftward and rightward directions, and a substantial amount of lateral pressure is reached at these ends, at least one of the seals at the ends of compartment 28 is ruptured, and the contents of compartments 28 and 30 are merged (solution 34) to create the cooling or heating effect.

Figure 3A:
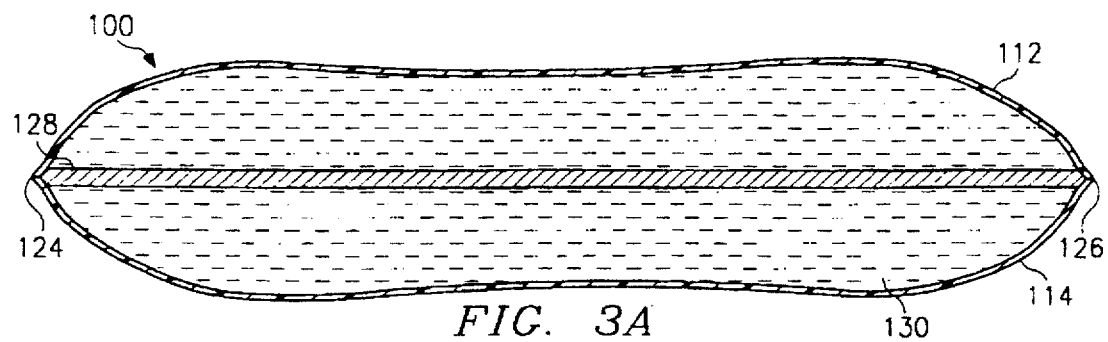
FIG. 3A is a side view of a hot or cold chemical therapy pack according to a second embodiment of the present invention.
Figure 3B:
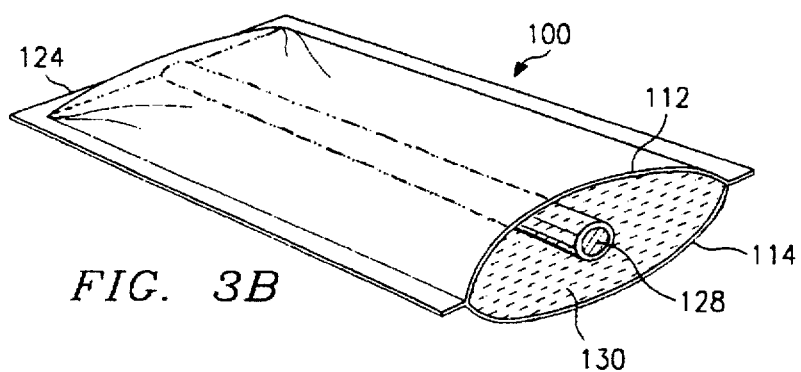
FIG. 3B is a perspective cut-away view of the hot or cold chemical therapy pack of FIG. 3A showing one compartment contained inside another compartment in accordance with the present invention.

FIG. 3 is a side view of a hot or cold chemical therapy pack according to a second embodiment of the present invention. FIG. 3A is a perspective cut-away view of the hot or cold chemical therapy pack of FIG. 3A showing one compartment contained inside another compartment in accordance with the present invention. Referring to FIG. 3, the construction of hot or cold pack 100 is similar to that of pack 10 shown in FIG. 2 (e.g., the pack is substantially extended in a non-collapsed configuration). For example, pack 100 is constructed with a pair of substantially rectangular-shaped sheets 112 and 114 of a relatively flexible, plastic or vinyl film material. Each of sheets 112 and 114 can be a film of material made of polyethylene, polypropylene, polyvinylchloride, or any one of a number of relatively strong, but pliable materials known and used in the heat or cold therapy art.

Sheets 112 and 114 are sealed to each other, along their peripheries, by a relatively strong heat seal. Again, heat sealing of these sheets is preferable, but any method of mechanically sealing sheets 112 and 114 along their peripheries can be used, such as the sealing methods described above with respect to pack 10. Preferably, sheets 112 and 114 are sealed to form a single compartment 130. Therefore, in the embodiment shown in FIG. 3, pack 100 is formed substantially in the shape of a bean-bag. Essentially, pack 100 can be any practical size or shape, such as, for example, oval-shaped, substantially circular in shape, or substantially rectangular in shape with rounded corners. Preferably, pack 100 is constructed without folds, such as the folds 16, 18, 20 and 22 of pack 10 in FIG. 1.

Pack 100 is preferably a liquid-filled vinyl or plastic bag. However, compartment 130 can be filled with a solid, chemical reactant, such as a reactant powder, or water soluble, exothermic or endothermic beads or "prills." In one aspect of the embodiment shown in FIG. 3, compartment 130 is filled with a liquid reactant such as, for example, the above-described mixture of water and aqueous ammonia.

During the initial fabrication of pack 100, compartment 130 is substantially filled with the liquid or solid reactant. The opposing ends of tubular compartment 128 are attached to, and sealed at, opposing ends 124 and 126 of the pack. When compartment 130 is filled with a liquid reactant, tubular compartment 128 can be filled with a complementary liquid or solid reactant which, when combined with the reactant in compartment 130, creates the desired exothermic or endothermic chemical reaction in pack 100. For example, if an endothermic reaction is desired, tubular compartment 128 can be filled with a plurality of water soluble beads of ammonium nitrate. As an alternative example, if an exothermic reaction is desired, the water soluble beads in tubular compartment 128 can be made of calcium chloride. Compartment 128 can contain prills, some structural and chemical equivalent of prills, or a chemical reactant "slurry." In yet a different aspect of the embodiment, compartment 128 can contain water or the mixture of water and aqueous ammonia, while compartment 130 contains the complementary reactant (e.g., water soluble beads, etc.). Tubular compartment 128 is preferably rupturable in that it may be constructed of a relatively flexible, plastic or vinyl material having a natural weak point at location 132 (or a rupturable seam). Alternatively, tubular compartment 128 can be constructed of a relatively rigid material that can be ruptured with substantial pressure at a sealed end 124 or 126.

Figure 4:
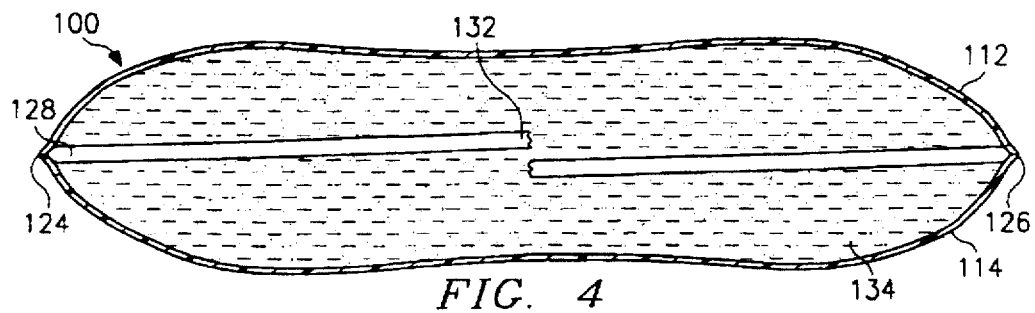
FIG. 4 is a side view of the hot or cold chemical therapy pack shown in FIG. 3 after the inner compartment has ruptured or broken at a weak point.

FIG. 4 is a side view of the hot or cold chemical therapy pack shown in FIG. 3 after the inner compartment has ruptured or broken at a weak point. Referring to FIGS. 3 and 4, in order to activate pack 100 for use, tubular compartment 128 is ruptured preferably at a natural weak point at location 132 (or at a seam) by applying pressure to, squeezing, or kneading compartment 130, so that the external pressure and/or torque applied to compartment 130 is transferred as lateral pressure, from the right and left ends of the pack towards its center, via the surface component of compartment 128 to the weak point at 132 or to a seam. Once a substantial amount of lateral pressure (e.g., the external pressure applied to the right and left sides of pack 100 to compress the pack) is reached at the seam or weak point 132, the seam or weak point is ruptured (FIG. 4) and the contents of compartments 128 and 130 are thus merged (solution 134) and mix together to react. Consequently, the desired endothermic or exothermic reaction is activated and pack 100 creates either a cooling or heating effect. Pack 100 can then be placed against the body part or item to be cooled or heated.

Although the present invention and its advantages have been described in detail, it should be understood that various changes, substitutions and alterations can be made therein without departing from the spirit and scope of the invention as defined by the appended claims.

What is claimed is:

1. A hot or cold chemical therapy pack, comprising:
   a first compartment containing a first reactant; and
   a second compartment contained in said first compartment, said second compartment containing a second reactant and including a first end attached to a first end of said first compartment and a second end attached to a second end of said first compartment, said second compartment including a rupturable weak point or seam.

2. The hot or cold chemical therapy pack according to claim 1, wherein said first and second reactants react endothermically upon contact.

3. The hot or cold chemical therapy pack according to claim 1, wherein said first and second reactants react exothermically upon contact.

4. A hot or cold chemical therapy pack, comprising:
   a first compartment containing a first reactant;
   a second compartment contained in said first compartment, said second compartment containing a second reactant and including a first end attached to a first end of said first compartment and a second end attached to a second end of said first compartment, said second compartment including a rupturable weak point or seam; and
   wherein said seam is located at one of said attachments of said first and second compartments.

5. The hot or cold chemical therapy pack according to claim 1, wherein said first compartment comprises a flexible, vinyl or plastic film material.

6. The hot or cold chemical therapy pack according to claim 1, wherein said second compartment comprises a tubular-shaped compartment.

7. The hot or cold chemical therapy pack according to claim 1, wherein said first compartment is arranged in a semi-collapsed configuration.

8. A hot or cold chemical therapy pack, comprising:
   a first sheet of a generally rectangularly-shaped material;
   a second sheet of a generally rectangularly-shaped material, each sheet having opposing upper and lower surfaces bound together by two longitudinal and two transverse edge surfaces, peripherally sealed adjacent the edge surfaces and defining a generally rectangularly-shaped sealed pack having a first compartment;
   a rupturable compartment contained in the first compartment of said sealed pack and extending from one longitudinal seal to the other longitudinal seal;

a first reactant contained in the first compartment of said sealed pack; and a second reactant contained in said rupturable compartment, said first and second reactants reacting exothermically or endothermically upon contact.

9. The hot or cold chemical therapy pack according to claim 8, wherein said peripherally sealed edge surfaces are heat sealed.

10. The hot or cold chemical therapy pack according to claim 1, wherein said seam is located between said attachments of said first and second compartments.

11. The hot or cold chemical therapy pack according to claim 1, said first compartment further comprising two opposing longitudinal and two opposing transverse edge surfaces forming a periphery seal around said first compartment, said longitudinal edge surfaces forming said first and second ends of said first compartment.

12. The hot or cold chemical therapy pack according to claim 11, wherein said second compartment is unrestrained by said two opposing transverse edge surfaces.

13. The hot or cold chemical therapy pack according to claim 11, wherein said second compartment is elongated a direction normal to the longitudinal edge surfaces.

14. The hot or cold chemical therapy pack according to claim 1, wherein said second compartment is suspended substantially along a middle of said first compartment.

15. The hot or cold chemical therapy pack according to claim 1, wherein said second compartment is elongated in a single direction.

16. The hot or cold chemical therapy pack according to claim 8, wherein said rupturable compartment comprises a tubular-shaped compartment.

17. The hot or cold chemical therapy pack according to claim 8, wherein said rupturable compartment is arranged in a semi-collapsed configuration.

18. The hot or cold chemical therapy pack according to claim 8, said rupturable compartment further comprising a rupturable weak point or seam.

19. A hot or cold chemical therapy pack, comprising:

a first sheet of a generally rectangularly-shaped material;

a second sheet of a generally rectangularly-shaped material, each sheet having opposing upper and lower surfaces bound together by two longitudinal and two transverse edge surfaces, peripherally sealed adjacent the edge surfaces and defining a generally rectangularly-shaped sealed pack having a first compartment;

a rupturable compartment contained in the first compartment of said sealed pack and extending from one longitudinal seal to the other longitudinal seal;

a first reactant contained in the first compartment of said sealed pack;

a second reactant contained in said rupturable compartment, said first and second reactants reacting exothermically or endothermically upon contact;

said rupturable compartment further comprising a rupturable weak point or seam; and wherein said seam is located at one of said one longitudinal seals.

20. The hot or cold chemical therapy pack according to claim 18, wherein said seam is located between said longitudinal seals.

21. The hot or cold chemical therapy pack according to claim 8, wherein said rupturable compartment is unrestrained by said two transverse edge surfaces.

22. The hot or cold chemical therapy pack according to claim 8, wherein said rupturable compartment is elongated a direction normal to the longitudinal edge surfaces.

23. The hot or cold chemical therapy pack according to claim 8, wherein said rupturable compartment is suspended substantially along a middle of said sealed pack.

24. The hot or cold chemical therapy pack according to claim 8, wherein said rupturable compartment is elongated in a single direction.

* * * * *